United States Patent [19]
Tsals et al.

[11] Patent Number: 5,858,001
[45] Date of Patent: Jan. 12, 1999

[54] CARTRIDGE-BASED DRUG DELIVERY DEVICE

[75] Inventors: Izrail Tsals, Sudbury, Mass.; Joseph Gross, Dublin, Ireland; Gilad Lavi, Holon, Israel

[73] Assignee: Elan Medical Technologies Limited, Athlone, Ireland

[21] Appl. No.: 763,311

[22] Filed: Dec. 10, 1996

Related U.S. Application Data

[60] Provisional application No. 60/008,499, Dec. 11, 1945.

[51] Int. Cl.$^6$ ........................................... A61M 5/00
[52] U.S. Cl. ........................................ 604/135; 604/232
[58] Field of Search ................... 604/131, 132, 604/134, 135, 140, 141, 143, 145, 156, 223, 233, 187, 218, 51, 232, 136, 137, 157

[56] References Cited

U.S. PATENT DOCUMENTS

| | | | |
|---|---|---|---|
| 2,390,246 | 12/1945 | Folkman | 604/232 |
| 2,408,323 | 9/1946 | Lockhart et al. | 128/220 |
| 2,545,017 | 3/1951 | Billingsley | 128/173 |
| 2,576,951 | 12/1951 | Lockhart et al. | 128/218 |
| 2,605,765 | 8/1952 | Kollsman | 128/218 |
| 2,880,723 | 4/1959 | Adams | 128/215 |
| 3,189,029 | 6/1965 | Stephens | 604/232 |
| 4,140,117 | 2/1979 | Buckles et al. | 128/213 |
| 4,403,987 | 9/1983 | Gottinger | 604/134 X |
| 4,522,622 | 6/1985 | Peery et al. | 604/191 |
| 4,627,445 | 12/1986 | Garcia et al. | 128/770 |
| 4,637,403 | 1/1987 | Garcia et al. | 128/770 |
| 4,684,365 | 8/1987 | Reinicke | 604/126 |
| 4,697,622 | 10/1987 | Swift et al. | 141/1 |
| 4,734,092 | 3/1988 | Millerd | 604/67 |
| 4,753,651 | 6/1988 | Eckenhoff | 424/449 |
| 4,886,499 | 12/1989 | Cirelli et al. | 604/131 |
| 4,902,278 | 2/1990 | Maget et al. | 604/132 |
| 5,070,886 | 12/1991 | Mitchen et al. | 128/771 |
| 5,079,421 | 1/1992 | Kundson et al. | 250/343 |
| 5,090,963 | 2/1992 | Gross et al. | 604/132 |

(List continued on next page.)

FOREIGN PATENT DOCUMENTS

| | | | |
|---|---|---|---|
| 0 098 592 | 1/1984 | European Pat. Off. | A61M 5/00 |
| 0 209 677 | 1/1987 | European Pat. Off. | A61M 5/14 |
| 0 401 179 | 12/1990 | European Pat. Off. | A61B 5/00 |
| 0 513 879 A2 | 11/1992 | European Pat. Off. | A61M 37/00 |
| 0 638 324 A1 | 2/1995 | European Pat. Off. | A61M 5/32 |
| 2 243 705 | 4/1975 | France | A61M 5/20 |
| 44 26 784 A1 | 2/1995 | Germany | 604/131 |
| 3430/87 | 12/1986 | Ireland | A61M 5/20 |
| 718837 | 11/1954 | United Kingdom . | |
| WO 89/12473 | 12/1989 | WIPO | A61M 5/20 |
| WO 91/00753 | 1/1991 | WIPO | A61M 31/00 |
| WO 92/11879 | 7/1992 | WIPO | A61M 1/08 |
| WO 93/17754 | 9/1993 | WIPO | A61N 1/30 |
| WO 94/07562 | 4/1994 | WIPO | A61M 31/00 |
| WO 95/10223 | 4/1995 | WIPO | A61B 5/00 |
| WO 96/25089 | 8/1996 | WIPO | A61B 5/00 |

*Primary Examiner*—John D Yasko
*Attorney, Agent, or Firm*—Kathleen L. Maher

[57] ABSTRACT

A liquid drug delivery device is adapted to be adhered to the skin of a subject by a base member defining a skin-contacting surface having an adhesive coating. A columnar cartridge serves as reservoir for the drug and is incorporated in a housing which is connected to the base member such that in use the longitudinal axis of the cartridge is disposed substantially parallel to the skin-contacting surface. A delivery needle communicating in use with the interior of the cartridge penetrates the skin of the subject when the housing snaps downward relative to the base member. This action also causes the actuation of a citric acid/sodium bicarbonate gas generator which generates a gas to move a piston within the cartridge, compressing the drug compartment. This compression causes a stopper to be penetrated by a conduit in communication with the delivery needle, allowing the drug to be ejected from the compartment through the needle and into the subcutaneous tissue of the subject.

31 Claims, 10 Drawing Sheets

U.S. PATENT DOCUMENTS

| | | | |
|---|---|---|---|
| 5,135,507 | 8/1992 | Haber et al. | 604/223 X |
| 5,156,591 | 10/1992 | Gross et al. | 604/20 |
| 5,267,963 | 12/1993 | Bachynsky | 604/134 |
| 5,279,544 | 1/1994 | Gross et al. | 604/20 |
| 5,318,557 | 6/1994 | Gross | 604/891.1 |
| 5,336,201 | 8/1994 | Von Der Decken | 604/223 |
| 5,354,264 | 10/1994 | Bae et al. | 604/21 |
| 5,368,578 | 11/1994 | Covington et al. | 604/187 X |
| 5,390,671 | 2/1995 | Lord et al. | 128/635 |
| 5,507,730 | 4/1996 | Haber et al. | 604/223 X |
| 5,545,143 | 8/1996 | Fischell | 604/180 |
| 5,562,613 | 10/1996 | Kaldany | 604/57 |
| 5,616,132 | 4/1997 | Newman | 604/140 X |

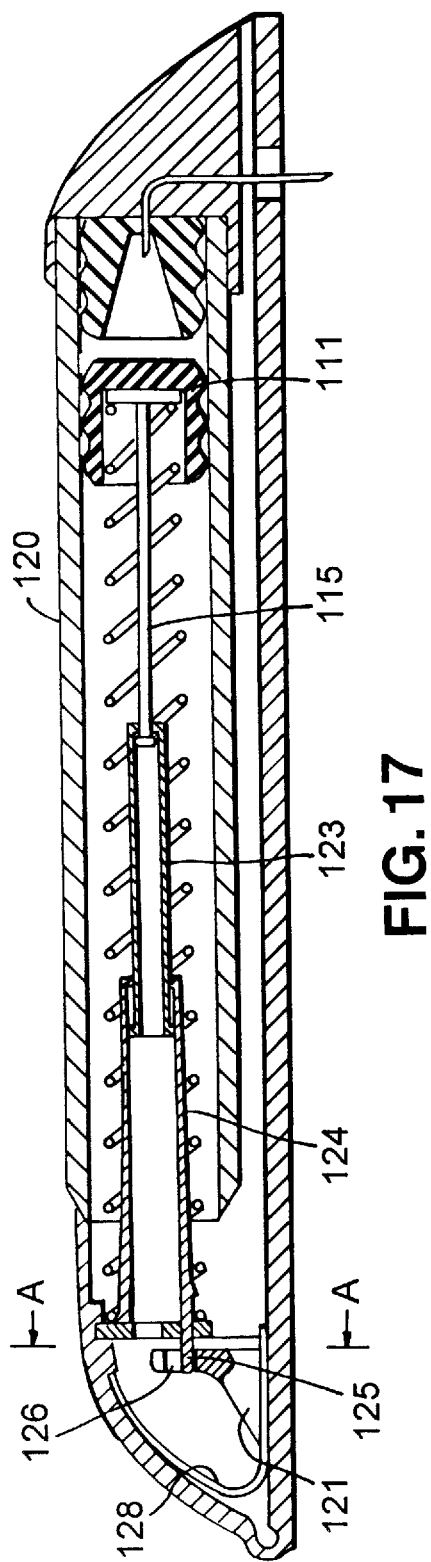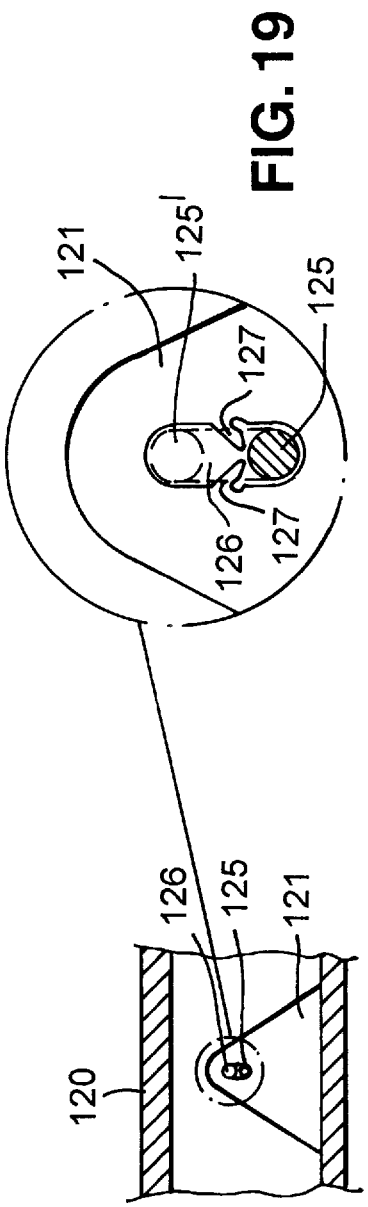

CARTRIDGE-BASED DRUG DELIVERY DEVICE

FIELD OF THE INVENTION

This is a provisional application Ser. No. 60/008,499, filed Dec. 11, 1945.

This invention relates to devices for subcutaneous, intravenous, intramuscular or intradermal delivery of drugs to a subject.

BACKGROUND OF THE INVENTION

The conventional method of parenteral administration of a drug to a subject is by injection using a hypodermic syringe. A number of difficulties associated with these syringes have led to attempts to derive more advantageous drug delivery devices. Syringes are not generally advocated for use in self administration by patients because of the dangers of embolisms arising from the introduction of air bubbles into the bloodstream, incorrect dosing, and the accidental infection of third parties after use of the syringe. In any event, syringes cannot be used by children or by many elderly patients, and the use of syringes is very traumatic for the large number of people who are needlephobic to a greater or lesser extent.

In trying to provide improved syringes, a number of inventors have focussed on the provision of a pre-filled syringe or a pre-filled ampoule for use in a syringe, as these devices can be useful in addressing the problems of incorrect dosage or incorrect filling of syringes. Furthermore, some syringes have been provided with expelling means which automatically deliver the drug from the syringe body or ampoule, rather than relying on a conventional syringe mechanism which can be difficult to manipulate in a smooth uniform fashion with one hand. Examples of such devices are the syringe disclosed in U.S. Pat. No. 2,390,246, the ampoule disclosed in U.S. Pat. No. 2,445,477 and the disposable needleless hypodermic injector disclosed in U.S. Pat. No. 3,527,212.

The devices of U.S. Pat. Nos. 2,390,246 and 2,445,477 still require the patient to correctly administer the injection, which may be difficult for some patients, and which some patients may refuse to do because of a fear of needles. Furthermore, each of these documents discloses a very sophisticated and complex mechanical arrangement for activating the expelling means. The devices would, in consequence, be prohibitively difficult and expensive to mass produce and would be prone to failure due to device complexity.

The device of U.S. Pat. No. 3,527,212 eliminates the use of needles and has a construction with fewer parts, but manufacture would still be difficult and expensive as the needleless injection of a drug requires the drug to be provided to the skin at pressures in excess of 400 lb/in$^2$ (27.5 bar). Thus, the device must be provided with a propellant at such a pressure when it is manufactured, and this pressure must be maintained throughout the shelf life of the device in a compartment which is bounded by a membrane strong enough to withstand the pressure but which is nevertheless easily rupturable by the manual depression of a plunger. Again, it will be appreciated that these requirements lead to a product which is quite difficult and expensive to manufacture.

Needleless devices have their own problems, since their correct use requires a certain degree of dexterity and strength. The device must be held firmly against the skin at the correct angle. Correct delivery of the drug requires it to be propelled at high pressure through the skin, so if the device is held at an incorrect angle or is not held firmly enough, then there is a strong likelihood that the medicament will not pass through the skin but will be dispersed into the air. As needleless injectors are usually quite bulky, the dexterity issue may be far from trivial from many patients.

Another limitation which is associated with each of the devices referred to above is that they can only be used for bolus administration, i.e. the immediate injection of a single entire dose. This is not suitable for all therapies, as it may be preferred in many cases to provide a continuous infusion of a drug both to avoid toxicity problems and to provide improved efficacy. Furthermore, if a drug is provided as a bolus injection, it may be necessary to inject a number of doses per day.

A number of infusion pumps are known, such as those described in U.S. Pat. No. 4,886,499 and our own WO 95/13838. In general, however, infusion pumps are far more sophisticated and complex than syringes or syringe-based injectors, with the result that they are unable to compete commercially with conventional injectors.

The problems associated with complex devices should not be underestimated from a manufacturing point of view. Not only does it become increasingly difficult and expensive to mass-produce a device having large numbers of components, but the reliability of such devices is inherently worse. To illustrate this point, if each component in a production line is tested and found to have, on average, a reliability of 99% (1 failure in every 100), then devices having only 5 components can be predicted to have expected reliability rates of 95% (given by $0.99^5$). Devices having 10, 20, and 50 of such components can be expected to have reliability rates of 90%, 82% and 61%, respectively. Evidently the safety implications of increasing device complexity cannot be ignored when considering drug delivery devices in particular.

Therefore, among the objects of the present invention are the provision of a drug delivery device which: is capable of delivering a pre-set dosage of drug to a subject; is suitable for use in self-administration by patients (including young patients and elderly patients); does not require the patient to consciously insert a needle into the skin; has a construction sufficiently simple to enable it to be mass produced at least as cheaply as (and in most cases more cheaply than) prior art bolus injectors described in the documents referred to above and substantially more cheaply than prior art infusion pumps; can provide either a bolus injection or can perform a continuous or controlled infusion; and overcomes the disadvantages associated with the conventional hypodermic syringe. Further objects and advantages of the invention will become apparent from the description given below.

SUMMARY OF THE INVENTION

Accordingly the invention provides a liquid drug delivery device comprising a base member defining a skin-contacting surface for application to the skin of a subject, a columnar cartridge serving as reservoir for the drug and which is connected to the base member such that in use the longitudinal axis of the cartridge is disposed substantially parallel to the skin-contacting surface, a delivery needle communicating in use with the interior of the cartridge and adapted to penetrate the skin of the subject, and means for expelling a drug out of the interior of the cartridge and through the skin of the subject via the delivery needle.

Because the device has a skin-contacting surface and a columnar cartridge disposed substantially parallel thereto, the device can be applied to the skin in order to effect delivery of the drug. One can use a conventional columnar cartridge such as a refill cartridge of the type used in "en-type" insulin injectors, or it can be any other type of columnar cartridge. Such cartridges may suitably be cylindrical glass or plastic cartridges, for example, and would preferably be extremely inexpensive to manufacture. The configuration of the device means it can be applied to the skin, and delivery can be effected in a single step application, as will be described below. The configuration which uses a skin-contacting surface and a delivery needle which penetrates the skin of the subject means that far less dexterity is required in administering the drug than is the case with many bolus injectors, including those referred to previously.

The term "cartridge" as used herein denotes a columnar container or vessel for a liquid, preferably formed of glass or plastic. The term "cartridge" does not necessarily imply a component which is removable from the device as a whole, or a component which is replaceable, although the cartridge may in fact be removable or replaceable.

The term "liquid drug" includes drugs which are in the form of liquids, a solutions, suspensions, or flowable gels.

Suitably, a portion of the interior of the cartridge defines a drug compartment for the drug, the drug being expelled from the compartment by a piston actuated by the expelling means.

It will be appreciated that when a piston is employed to expel the drug the columnar cartridge may be cylindrical or it may be of generally cylindrical form (the cross section need not be circular). Indeed, one can envisage cases where a cylinder having a slight longitudinal curve would be employed for design reasons. Such cartridge shapes are perfectly acceptable provided of course that the piston is still effective to expel the drug from the drug compartment.

Preferably, the interior of the cartridge also defines a chamber housing the expelling means, such that the actuation of the piston by the expelling means causes the expansion of said chamber and the contraction of said drug compartment.

This arrangement is advantageous because the cartridge (which may be as simple as a glass or plastic cylinder) can house both the drug and the expelling means. Indeed, a number of embodiments described in detail below illustrate this arrangement. By incorporating the expelling means into the cartridge, one obtains significant savings in space, thereby making the device as small and unobtrusive as possible. This is particularly important if the device is to be worn for an extended period of time.

One can also envisage embodiments in which the expelling means is incorporated within the cartridge but the chamber containing the expelling means is in fact also the drug compartment and the expelling means serve to pull the piston and contract the chamber (and drug compartment). There are practical disadvantages associated with this arrangement given that the expelling means must be sterile and inert if it is in contact with the drug. For practical purposes it is preferable to use the piston to separate an expansible chamber for the expelling means and a contractible drug compartment for the drug.

Suitably, the device is provided with a conduit enabling fluid communication to be established in use between the drug compartment and the delivery needle.

Preferably, the conduit extends at substantially right angles from the delivery needle.

By having a delivery needle having a conduit extending at substantially right angles from the delivery needle, the conduit can access the drug compartment through an end of the cartridge (in a direction purposely parallel to the skin-contacting surface), and the delivery needle can deliver drug passing out of the drug compartment through the conduit by penetrating normally through the skin. Clearly, an angle of exactly 90° is not required (although it may be preferred), but one would envisage that the conduit extends from the delivery needle at 80°–100°, preferably 85°–95° (and most preferably 90°). This allows the needle to penetrate the skin vertically and simultaneously allows communication to be established between this delivery needle and a cartridge lying exactly parallel to the skin.

Preferably, the conduit is integral with the delivery needle.

Suitably, the delivery needle and the conduit form part of a needle assembly mounted on an end of the cartridge.

In preferred embodiments, the device further comprises a mechanism for actuating the expelling means.

Suitably, the connection between the cartridge and the base member allows relative movement therebetween from an initial configuration to a working configuration.

Preferably, said relative movement operates the mechanism for actuating the expelling means.

In other words, the device can be in an initial configuration in which it is maintained during storage or before use, and then by moving the cartridge and base member relative to one another, the device is primed for use and the expelling means is actuated.

Further, preferably, said relative movement causes the delivery needle to project through the plane of the skin-contacting surface and thereby penetrate the skin in use.

This arrangement allows the skin-contacting surface to be placed on the skin (this surface being suitably provided with an adhesive coating or the device being provided with some other means of retaining the skin-contacting surface on the skin), and then a relative movement between the base member and the cartridge causes the penetration of the skin (and optionally, the actuation of the expelling means).

Further, preferably, said relative movement causes the establishment of fluid communication between the drug compartment and the delivery needle.

If the relative movement between the cartridge and base member accomplishes all three preferred acts, namely the actuation of the expelling means, the penetration of the skin by the delivery needle and the establishment of fluid communication between the drug compartment and the delivery needle, then one can achieve a single-step application of the device, whereby some movement between the cartridge and the base member achieves the delivery of drug in a safe and predictable manner. The relative movement may be rotational or translational. For example, the cartridge could be incorporated in a first section of a housing which is screwed relative to a second section of the housing (the second section incorporating the base member), with this screwing movement initiating delivery.

Alternatively, the connection between the cartridge and the base member is provided by a hinge enabling the cartridge and the base member to be pressed towards one another from a spaced-apart initial configuration to an adjacent working configuration.

Suitably, the skin-contacting surface is provided with an aperture through which the delivery needle extends in use.

If the cartridge is movable relative to the base member, the needle can be retracted in the initial configuration and it can extend through the skin-contacting surface in the working configuration; this allows for a device in which the needle is never seen by the subject in normal use. This is particularly suitable for needlephobics or people who, while not actually needlephobic, are upset to a greater or lesser degree by needles and injections.

Preferably, an end of the cartridge is provided with a stopper and the conduit and stopper are movable relative to one another to allow the conduit to penetrate through the stopper and thereby establish said communication.

The conduit can be pointed or blunt, provided that it is able to penetrate through and establish communication with the interior of the cartridge.

This arrangement is advantageous because it allows the contents of the drug compartment to be maintained in a sterile condition until the moment when communication is established between the delivery needle and the drug compartment. As described above, and as further described in detail below, the device can be applied to the skin and a single action can cause establishment of communication between the delivery needle and the cartridge at roughly the same moment as the delivery needle penetrates the skin. Thus, sterility is ensured from the point of view of the patient. The skin-contacting surface may be covered before use by a release liner of some sort.

According to one embodiment, the position of the needle assembly is fixed with respect to the cartridge, and the stopper is movable relative to both the cartridge and the needle assembly.

Suitably, the actuation of the expelling means causes the stopper to be pressed onto and penetrated by the conduit.

According to another embodiment, the position of the stopper is fixed with respect to the cartridge, and the needle assembly is movable relative to both the cartridge and the stopper.

In certain embodiments, the expelling means comprises a precompressed spring.

Preferably, the mechanism for actuating the expelling means comprises a catch which when released enables the pre-compressed spring to relax.

Most preferably, a relative movement between the cartridge and the base member from an initial configuration to a working configuration causes the catch to be released.

Alternatively, the expelling means comprises a gas generator which generates a gas when two or more reactants are brought into contact.

Suitably, the gas generator comprises at least one liquid.

Advantageously, the gas generator comprises the components of an effervescent couple.

Again, alternatively, the expelling means comprises a material which swells in the presence of a liquid, and also comprises a supply of said liquid.

Suitably, in such cases, said material is a swellable gel and said liquid is water.

Suitably, in embodiments where the expelling means comprises a liquid as an essential component, and when the cartridge and base member are movable relative to one another as described above, said liquid is contained within a rupturable compartment and the mechanism for actuating the expelling means comprises a penetrating member, the penetrating member and the rupturable compartment being moved relative to one another upon the relative movement of the cartridge and the base member, so as to cause the penetration of said rupturable compartment and the actuation of the expelling means.

Suitably, the device further comprises a snap mechanism which maintains a stable initial configuration and a stable working configuration and which when actuated causes the device to snap from said initial configuration to said working configuration.

Further, suitably, the device is provided with resilient means biasing the device to said initial configuration and means for disengaging said snap mechanism when delivery has been completed.

Preferably, said disengaging means comprises a member linked to said piston such that when the piston has completed the expulsion of drug from the drug compartment, said member is caused to move and said movement causes the disengagement of said snap mechanism, such that said resilient means causes the device to resume said initial configuration.

Thus, if the device is provided with both a snap mechanism and a spring biasing the device to the initial configuration, the automatic release of the snap mechanism after completion of delivery causes the spring to return the device to the initial configuration (being no longer held in the working configuration by the snap mechanism). Suitably, this movement will cause the retraction of the delivery needle from the skin, optionally to a point where it is no longer visible.

This action (which might be observed by the cartridge snapping away from the base member) informs the subject that delivery has been completed and, in certain cases, retracts the needle to the point where it is concealed from the subject both before use and after use.

Suitably, said relative movement is a pivotal movement.

Preferably, the cartridge and base member are connected by means of a hinge.

According to a further embodiment, said delivery needle projects through the plane of the skin-contacting surface at or outside of the periphery of the skin-contacting surface.

It is preferred if the delivery needle projects through the plane at a point on the periphery of the skin-contacting surface distal from the hinge, as this means that the needle will jab through the skin more quickly than it would if it was located right beside the hinge. The quicker the needle pierces the skin the less painful it is likely to be for the subject.

According to one embodiment, the delivery needle is in the shape of a segment of arc of an imaginary circle, said circle having a radius equal to the distance between the delivery needle and the hinge and lying in a plane which is substantially normal to the plane of the skin-contacting surface.

This embodiment with a curved needle is useful where the needle is unusually long, as a pivotal movement such as that provided by a hinge causes the needle to have a lateral component of velocity when it is penetrating the skin. This lateral movement of the needle causes the stretching or tearing of the skin in extreme cases, and in any event leaves a bigger entry wound than would otherwise be the case. The dimensions of the imaginary circle given above ensure that the body of the needle exactly follows the point of the needle on its path into the subject.

Alternatively, the delivery needle may be straight. This is preferred in embodiments in which delivery needle moves straight down into the skin, or in embodiments where the length of the delivery needle or the radius of the imaginary circle means that the needle has a negligibly small lateral component of movement upon entering the so skin that it would be uneconomical or unnecessary to make a curved needle. Indeed, in many cases, it will be unnecessary for the needle to be curved.

Typical medicaments suitable for use with the device according to the invention include peptides, proteins or hormones such as insulin, calcitonin, calcitonin gene regulating protein, atrial natriuretic protein colony stimulating factor, betaseron, erythropoietin (EPO), interferons such as a, b or g interferon, somatropin, somatotropin, somatostatin, insulin-like growth factor (somatomedins), luteinizing hormone release hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorphone, methodone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondanesetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in the treatment of heart disorders, and analogues thereof; sedatives such as benzodiazepines, phenothiozines, and analogues thereof; narcotic antagonists such as naltrexone, naloxone, and analogues thereof; chelating agents such as deferoxamine, and analogues thereof; anti-diuretic agents such as desmopressin, vasopressin, and analogues thereof; antianginal agents such as nitroglycerine, and analogues thereof; anti-neoplastics such as 5-fluorouracil, bleomycin, and analogues thereof; prostaglandins and analogues thereof; chemotherapy agents such as vincristine, and analogues thereof; and oligonucleotides such as antisense oligonucleotides.

BRIEF DESCRIPTION OF THE DRAWINGS

The invention will now be further described by the following descriptions of embodiment thereof, given by way of example only, with reference to the accompanying Drawings, in which:

FIG. 17 is a sectional elevation of the device of FIG. 16, when delivery has almost been completed;

FIG. 18 is a cross-sectional elevation of the device of FIG. 17, taken along the line A—A;

FIG. 19 is an enlarged view of a detail of FIG. 18;

DETAILED DESCRIPTION OF THE INVENTION

Figure 1:
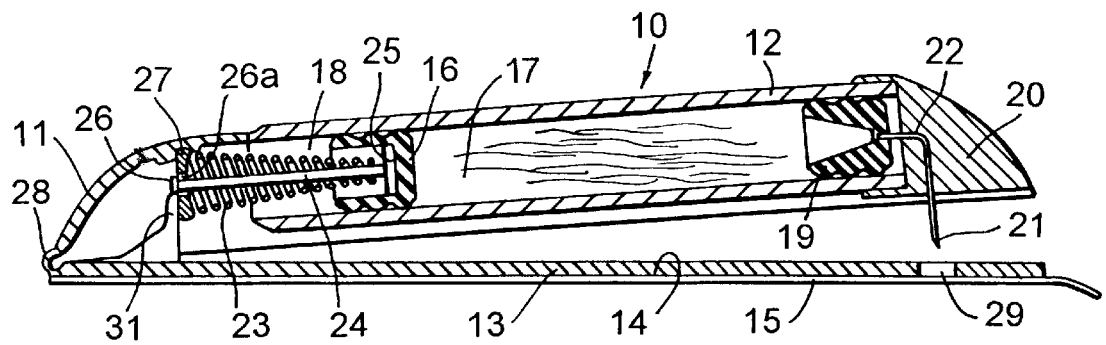
FIG. 1 is a sectional elevation of a cartridge-based drug delivery device according to the invention, before use.

In FIG. 1 there is indicated, generally at 10, a cartridge-based drug delivery device according to the invention. Device 10 is in the form of a body 11 comprising a cartridge 12 and a member 13 defining a skin contacting surface 14. Surface 14 is covered by a release liner 15 before use.

A piston 16 is contained in cartridge 12 and defines on one side thereof a drug compartment 17 and on the other side thereof a driving chamber 18. Compartment 17 is filled with a liquid drug and is sealed at the end opposite piston 16 by a stopper 19. A needle assembly 20 is mounted on cartridge 12. Needle assembly 20 has a hollow delivery needle 21 extending therefrom, and delivery needle 21 is provided with communication means in the form of a conduit needle 22. As illustrated in FIG. 1, conduit needle 22 penetrates into but not through stopper 19 before use.

A spring 23 is held under compressed tension by a rod 24 having a plate 25 at one end thereof and a catch projection 26 at the other end thereof. Rod 24 extends through an orifice 26a in a wall section 27 and catch projection 26 is retained by wall section 27 such that spring 23 is held under tension as long as catch projection 26 remains in position. Plate 25 abuts against piston 16.

Cartridge 12 is connected to member 13 by means of a living hinge 28. A simple snap mechanism (not shown) causes device 10 to remain in the configuration illustrated in FIG. 1 until cartridge 12 and member 13 are compressed together giving rise to the working configuration illustrated in FIG. 2. An aperture 29 in skin-contacting surface 14 allows needle 21 to project therethrough, thereby permitting cartridge 12 and member 13 to be pressed together such that, in use, cartridge 12 lies substantially flat against skin-contacting surface 14.

Figure 3:
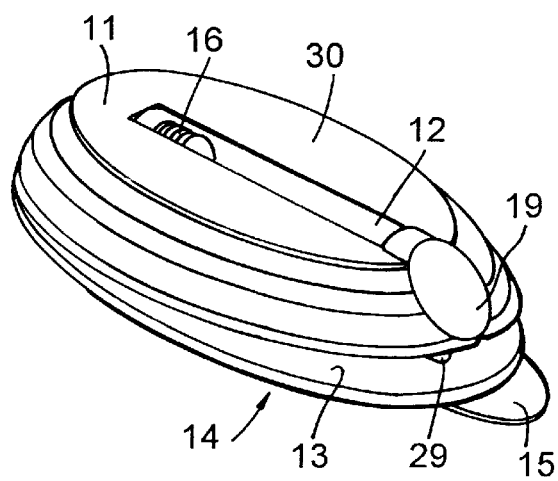
FIG. 3 is a perspective view of the device as illustrated in FIG. 1.

The operation of the device can be explained as follows. Before use, the device is in the configuration shown in FIG. 1. FIG. 3 shows a perspective view of device 10 in the same configuration, in which body 11, cartridge 12, member 13, release liner 15, piston 16, needle assembly 20 and aperture 29 can be seen. Immediately before use, release liner 15 is peeled away from skin-contacting surface 14, and skin contacting surface 14 is then placed against the skin to which it adheres by means of an adhesive coating. Downward pressure is then exerted on the upper surface 30 (see FIG. 3) of body 11 causing cartridge 12 to be snapped towards member 13 by means of hinge 28 and the snap mechanism (not shown). Delivery needle 21 passes through aperture 29 and penetrates through the skin.

Figure 2:
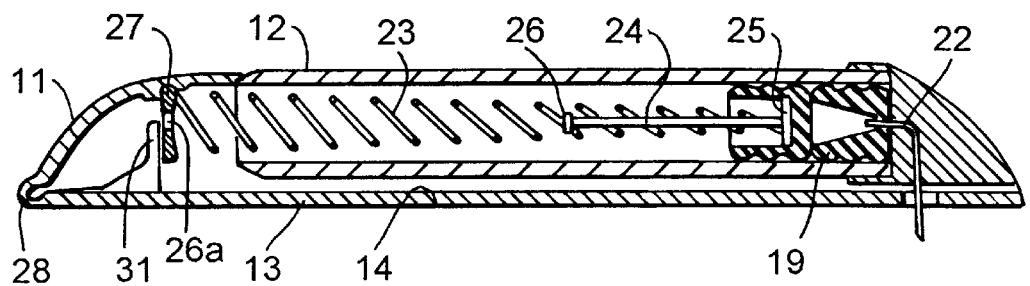
FIG. 2 is a section elevation of the device of FIG. 1, in use.

It can be seen in FIG. 1 that catch projection 26 rests against an abutment 31 before use. Referring to FIG. 2, it can be seen that when cartridge 12 has been snapped towards skin contacting surface 14, wall section 27 moves relative to abutment 31. Because wall section 27 moves downwards and catch projection 26 is prevented from moving downwards by abutment 31, the relative movements of wall section 27 and catch projection 26 cause catch projection 26 to be dislodged enabling it to pass through orifice 26a in wall section 27, which it does readily as spring 23 is under compressed tension. Once catch projection 26 is released, spring 23 urges rod 24 to move towards the position shown in FIG. 2.

This movement of rod 24 causes plate 25 to push piston 16 so as to compress drug compartment 17. As the liquid filling compartment 17 is incompressible, the pressure is transmitted to stopper 19 which moves towards needle assembly 20 such that conduit needle 22 penetrates completely through stopper 19, thereby effecting communication between compartment 17 and delivery needle 21. This creates an outlet from compartment 17 (namely via the delivery needle 21 into the skin, subcutaneous tissue or cardiovascular system of the subject to whom the drug is being delivered), thereby permitting piston 16 to continue to move forward under the urging of spring 23 (via plate 25), which causes the contraction of compartment 17 and the ejection of the liquid drug therefrom. Piston 16 moves forward until it meets stopper 19, at which point the reservoir is effectively empty and the device can be removed from the skin.

Removal of the device from the skin merely involves pulling body 11 upwards to remove delivery needle 21 from the skin, and peeling skin contacting surface 14 away from the skin. The use of a snap mechanism means that cartridge 12 and member 13 disengage from one another (i.e. body 11 snaps back to its original configuration as illustrated in FIGS. 1 and 3) before skin contacting surface 14 is peeled off the skin. This disengagement has the result that when removed, device 10 is harmless because delivery needle 21 has been retracted through aperture 29 and is thereby concealed, preventing accidental injury and possible risk of infection from delivery needle 21.

While the description of operation given above details the operation of the mechanism at some length, the actual operation from the patient's point of view is as follows. Firstly, the release liner is peeled away to reveal a sterile adhesive surface. Secondly, the device is pressed against the skin by applying pressure to top surface 30. This act causes (i) the adhesion of skin contacting surface 14, (ii) the snapping together of cartridge 12 and member 13, (iii) the resulting dislodgement of catch projection 26, which leads to (iv) the penetration of stopper 19 by conduit needle 22 and (v) the delivery of the contents of compartment 17 through delivery needle 21. After delivery, body 11 is lifted away from the skin. This act causes the retraction of needle 21, thereby making the device safe for disposal.

All the patient has to do, therefore, is: (a) peel away the release liner, (b) press the device against the skin, and (c) lift the device off the skin when delivery has been completed. The completion of delivery can be observed by monitoring the movement of piston 16 along the length of cartridge 12 (see FIG. 3).

All of the steps relating to correctly administering a precise dosage of drug are accomplished by the single step (b), namely applying pressure to upper surface 30. This simplicity opens up the possibility of self administration by patients who would be unable or unwilling to self administer a drug otherwise. The configuration of device 10 not only ensures that the entire mechanism is activated by a single step, but it also compels the patient to administer the drug correctly. The mechanism causes delivery needle 21 to penetrate the skin at the correct angle and to the correct depth, and since cartridge 12 is prefilled with a known volume of drug, the metering of the dose to be delivered is automatic and is removed from the patient's responsibility.

Furthermore, while other drug delivery devices are known which can be applied to the skin such that a needle correctly penetrates the skin and such that the drug is delivered upon application of the device, the structure and mode of operation of the device shown in FIGS. 1–3 is much simpler than for known devices. Manufacturing costs are significantly lowered, and the risks of malfunction or patient error are clearly reduced by simplifying the construction and operation of the device.

A further advantage provided by the device of FIGS. 1–3 is that from the patient's point of view, the needle is invisible. This is a distinct advantage for subjects who are uncomfortable with the idea of injections and needles. The diameter of the needle used in the embodiment of FIGS. 1–3 is 0.25 mm, making it sufficiently small that it is effectively painless when it penetrates the skin. The internal diameter is nevertheless big enough to allow the delivery of macromolecular compounds such as peptides, polypeptides and proteins. Although device 10 as shown in FIGS. 1–3 does not entirely conceal delivery needle 21 (which can be seen by looking into the gap between member 13 and cartridge 12), a collar can be provided around the periphery of skin contacting surface 14 so as to conceal the needle at all times, if the visibility of the needle is a major concern.

Figure 4:
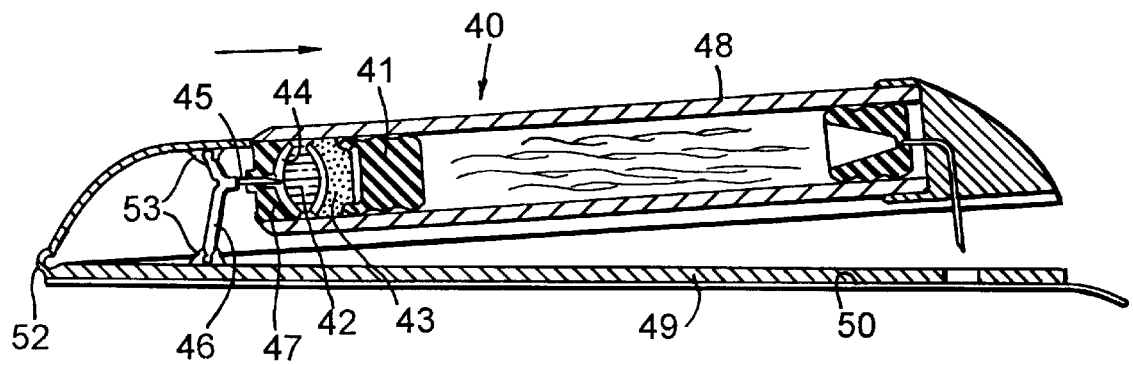
FIG. 4 is a sectional elevation of a second embodiment of a device according to the invention, before use.
Figure 5:
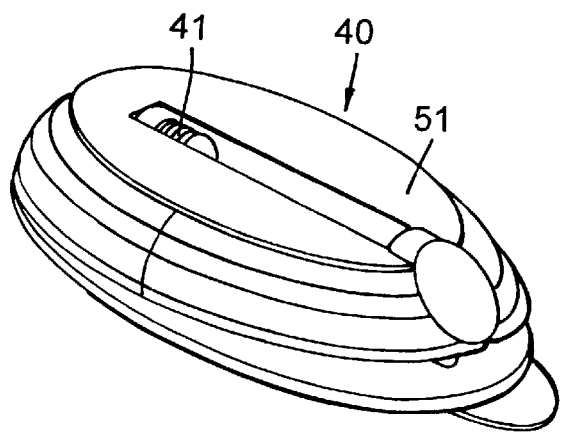
FIG. 5 is a perspective view of the device of FIG. 4.

Referring now to FIG. 4, there is indicated, generally at 40, a different embodiment of a drug delivery device according to the invention. Device 40 is in many respects similar to device 10 of FIGS. 1–3, but a different expelling means is employed and a different mechanism for actuating the expelling means is employed. In device 40, piston 41 is driven by gas pressure. Gas is generated by the reaction of a quantity of citric acid solution 42 with a sodium bicarbonate tablet 43. In FIG. 4, device 40 is illustrated before use (a perspective view can be seen in FIG. 5). Citric acid solution 42 is contained within a compartment defined by a rupturable membrane 44. A solid needle 45 is disposed with its point immediately adjacent to membrane 44. Needle 45 projects from a wishbone structure 46 through a stopper 47. Stopper 47 and piston 41 form a sealed compartment such that the generation of gas causes piston 41 to move in the direction indicated by the arrow.

The gas generator 42,43,44 is actuated by pressing the cartridge 48 and member 49 (which defines a skin-contacting surface 50) together. In practice this is done by placing surface 50 against the skin and pressing downwards on upper surface 51 (see FIG. 5). When cartridge 48 and member 49 are pressed together (via the flexing of a hinge 52) a pair of brackets 53 supporting wishbone structure 46 also approach one another. Wishbone structure 46 is flexible, so the movement of the brackets 53 causes wishbone structure 46 to flex, thereby moving needle 45 in the direction indicated by the arrow. This movement ruptures membrane 44, thereby releasing citric acid 42 which contacts sodium bicarbonate 43 and generates a gas to provide a driving force equivalent to spring 23 of device 10 illustrated in FIGS. 1–3.

Figure 6:
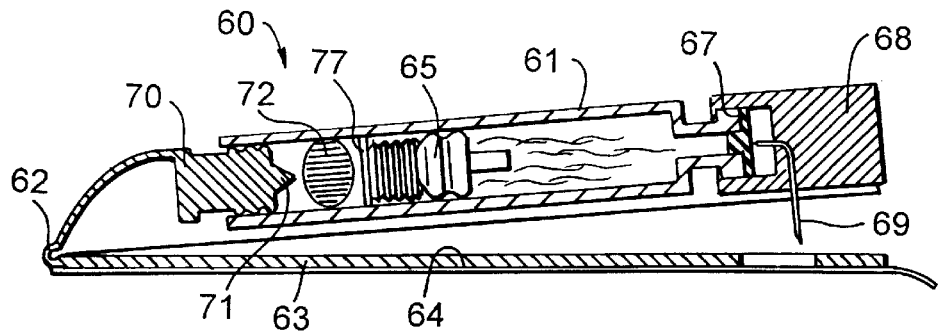
FIG. 6 is a sectional elevation of a third embodiment of a device according to the invention, before use.
Figure 7:
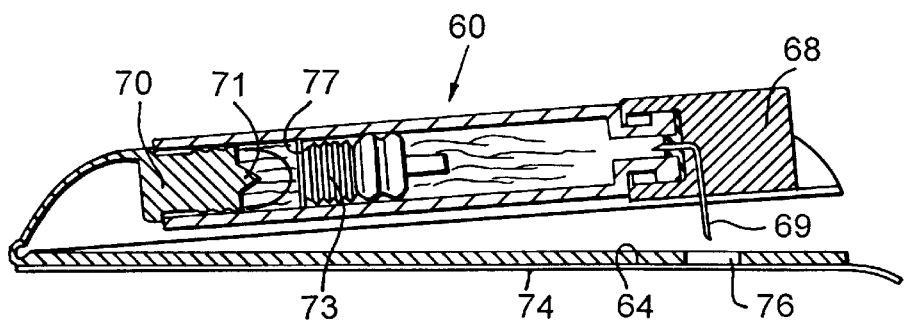
FIG. 7 is a sectional elevation showing the device of FIG. 6 when it has been primed and is ready for use.
Figure 8:
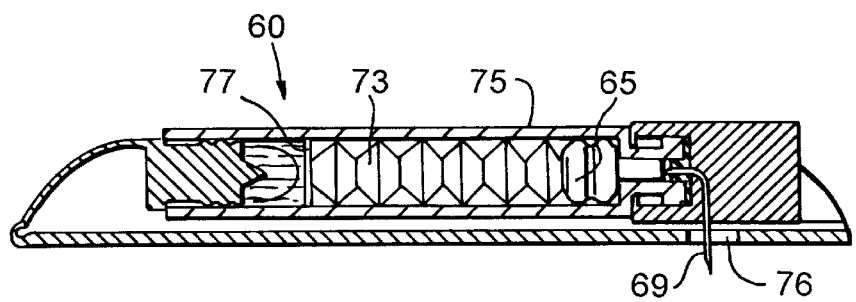
FIG. 8 is a sectional elevation of the device of FIGS. 6 and 7, when delivery has been completed.
Figure 9:
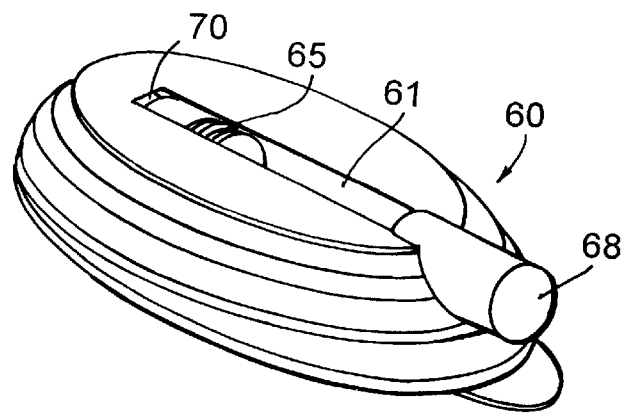
FIGS. 9–11 are perspective views of the device as illustrated in FIGS. 6–8, respectively.
Figure 10:
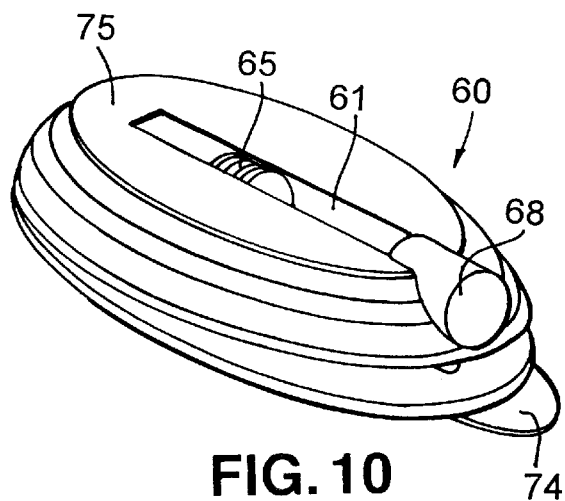
Figure 11:
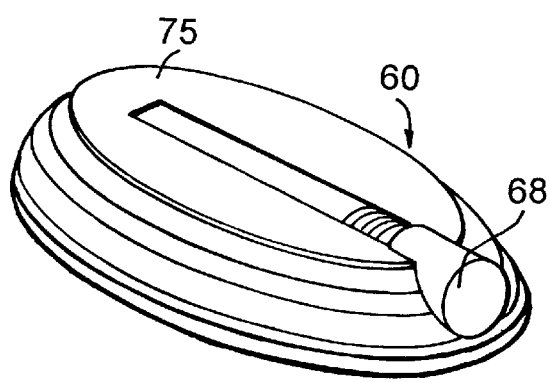

Referring now to FIGS. 6–11, one can see a further embodiment of the invention. FIGS. 6, 7 and 8 illustrate the device in sectional elevation, and FIGS. 9,10 and 11 are perspective views of the device as illustrated in FIGS. 6, 7 and 8, respectively.

Referring first to FIG. 6, the device, indicated generally at 60 has many features in common with the devices previously described. In particular, there is a cartridge 61 connected by a hinge 62 to a member 63 defining an adhesive skin-contacting surface 64. A piston 65 defines a drug compartment 66 which is sealed by a stopper 67.

A needle assembly 68 is moveable with respect to cartridge 61 in the direction indicated by the arrow so as to pierce stopper 67 and thereby provide communication between drug compartment 66 and a delivery needle 69, as illustrated in FIG. 7.

Pressure in the direction indicated by the arrow also causes cartridge 61 to move relative to a mounting member 70 on which cartridge 61 is slidably mounted. Member 70 is provided with penetrating means 71. When cartridge 61 moves in the direction indicated by the arrow relative to member 70, penetrating means 71 pierces a compartment 72 to release a quantity of water.

Referring to FIG. 7, it can be seen that a perforated polyethylene bellows 73 is wetted by the water released from compartment 72. Bellows 73 is water permeable and is filled with a gel which swells in the presence of water, such as acrylite gels. The choice of gel material determines to a large extent the rate of delivery. The delivery rate is also affected by the permeability of the bellows. The permeability of the bellows may be determined by the number and size of perforations or by the nature of the material (which may be water permeable) used for the bellows.

When needle assembly 68 has been pushed back to the extent indicated in FIGS. 7 and 10, the device is primed, at which point the release liner 74 is peeled away, skin-contacting surface 64 is pressed against the skin, and then pressure is applied to upper surface 75 (FIGS. 8 and 11) such that delivery needle 69 emerges through aperture 76 and penetrates the skin of the subject. Delivery is effected by the expansion of bellows 73 (when wetted) to drive piston 65 (see FIG. 8).

The device of FIGS. 6–11 is not shown to scale as the degree of expansion shown in FIG. 8 would not be achieved by a bellows and water compartment of the size shown in FIGS. 6 and 7. However, the principle of a permeable, gel-filled bellows expanding as water is absorbed by the gel is clear.

A freely permeable barrier 77 is provided between mounting member 70 and bellows 73. Barrier 77 is fixed relative to the cartridge, and so when compartment 72 is pierced and bellows 73 begins to expand as it absorbs water, barrier 77 prevents bellows 73 from expanding backwards into the space formerly occupied by the water in compartment 72. Although cartridge 61 is firmly mounted on mounting member 70, the seal between cartridge 61 and mounting member 70 is vacuum tied. A small amount of leakage is allowed for, to allow air to be drawn into the space between mounting member 70 and barrier 77 as the water is drawn out of that space by absorption into bellows 73. The degree of leakage is small enough, however, to prevent water from seeping out (this is perfectly possible given the differences in properties between water and air). As an alternative, a gas-permeable, water impermeable material could be used for mounting member 70 (or a section thereof).

An important difference between the devices of FIGS. 1–5 on the one hand and the device of FIGS. 6–11 on the other hand is that whereas spring 23 (in FIGS. 1–3) relaxes rapidly to provide a bolus delivery of drug, and gas generator 42,43,44 (in FIGS. 4 and 5), when actuated, generates a gas quickly over a short period of time to give bolus delivery, the swelling gel mechanism of FIGS. 6–11 provides a slow continuous expansion. Accordingly, whereas device 10 of FIGS. 1–3 and device 40 of FIGS. 4 and 5 act as bolus injectors, device 60 of FIGS. 6–11 acts as an infusion pump which can be used to deliver drug over a period dictated by the design of the device. It generally delivers all of the drug over an extended period of time, equivalent to the delivery provided by an infusion pump (for example, such as over a 12 hour, 24 hour or 48 hour period).

Figure 12:
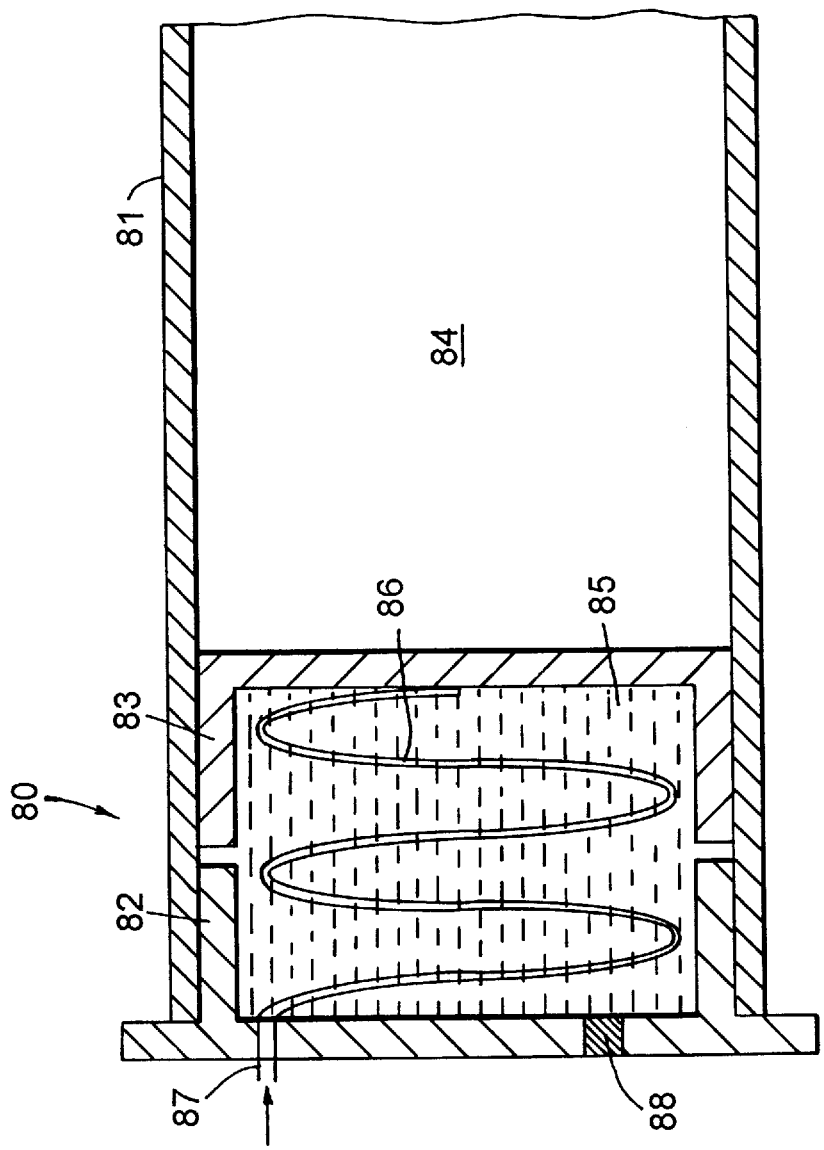
FIG. 12 is a section elevation of an alternative expelling means for use in a device according to the invention.

Referring next to FIG. 12, a further expelling means is indicated, generally at 80. Expelling means 80 is again positioned at an end of a cartridge 81. The expelling means 80 consists essentially of a fixed end cap 82 and a moveable end cap 83 which is slidable within cartridge 81 and which serves as a piston to compress drug compartment 84. Between them, the end caps 82,83 define a driving chamber which is filled with a swellable gel 85. A flexible perforated spiral wound plastics tube 86 also extends within the space defined by the end caps 82,83, and tube 86 is in communication, in use, with a source of water (not shown) via an inlet 87 in end cap 82. When water enters tube 86, it is free to enter gel 85 via perforation in tube 86. Gel 85 expands when it absorbs the water and because gel 85 continues to absorb water as it expands, water is continually drawn in via inlet 87. The expansion of gel 85 causes end cap 83 to slide within the interior of cartridge 81 thereby compressing drug compartment 84 and ejecting a liquid drug contained therein through an outlet, as described in relation to previous embodiments.

Figure 13:
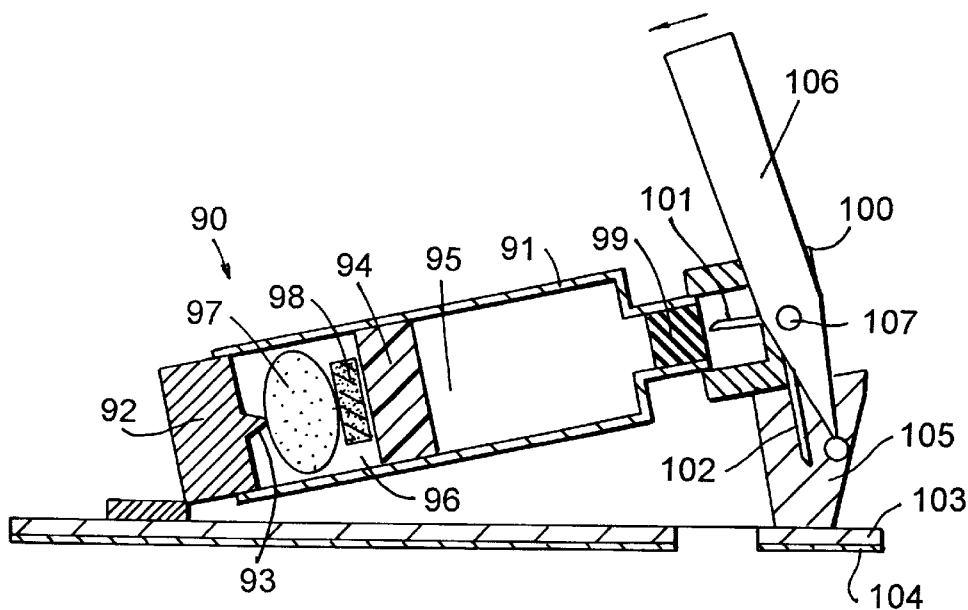
FIGS. 13–15 are schematic representations of a fourth embodiment of the device in successive stages of being applied to the skin of a subject.
Figure 14:
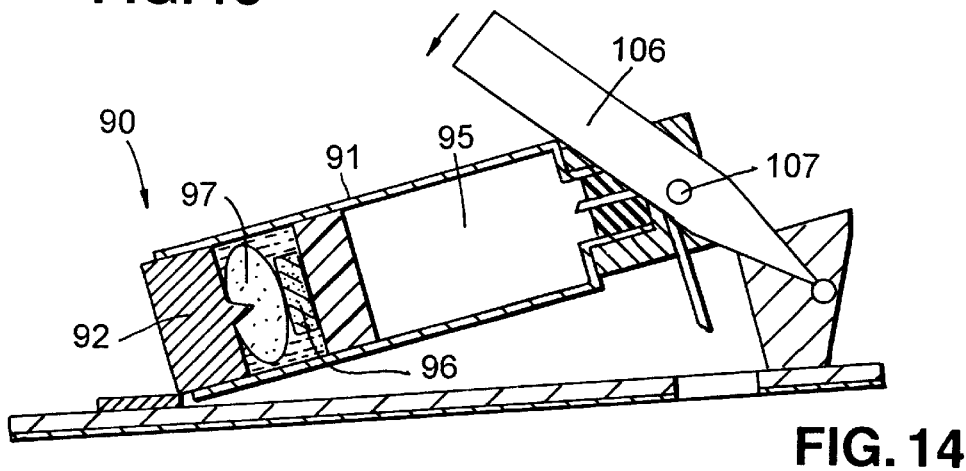
Figure 15:
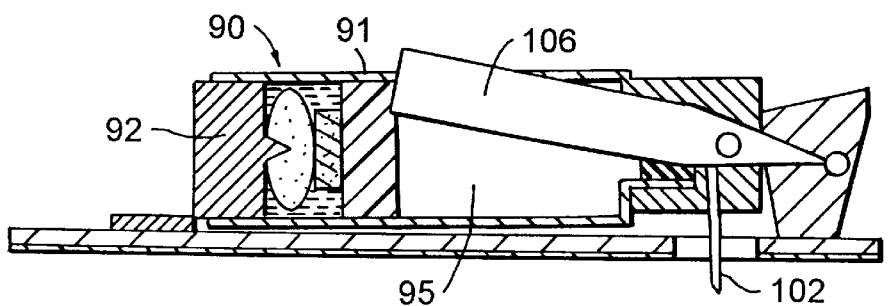

FIGS. 13–15 illustrate a schematic diagram of a further embodiment of the invention. It will be noted that the device indicated generally at 90 has many features in common with devices previously described. In particular, there is a cartridge 91 slidably mounted on a mounting member 92 provided with penetrating means 93. A piston 94 defines a drug compartment 95 on one side thereof and a driving chamber 96 on the other side thereof. Driving chamber 96 contains a rupturable citric acid compartment 97 and a sodium bicarbonate tablet 98 such that when compartment 97 is penetrated by penetrating means 93, citric acid is released to sodium bicarbonate tablet 98 in order to generate a gas and drive piston 94 along cartridge 91.

The end of drug compartment 95 opposite piston 94 is sealed by a penetrable stopper 99. A needle assembly 100 which has a hollow conduit needle 101 extending at right angles from a hollow delivery needle 102 is mounted on cartridge 91 such that movement of needle assembly 100 in the direction indicated by the arrow causes conduit needle 101 to pierce stopper 99, thereby establishing communication between drug compartment 95 and delivery needle 102.

Mounting member 92 is connected by a hinge to a base member 103 which defines a skin-contacting surface 104. Base member 103 is provided with a lever mounting 105 on which a lever 106 is pivotally mounted. Actuation of lever 106 in the direction indicated by the arrow in FIG. 13 causes the device to assume the configurations shown in FIG. 14 (initially) and FIG. 15 (subsequently). Actuation of lever 106 pushes needle assembly 100 (to which lever 106 is pivotally mounted by means of a pivot 107) onto cartridge 91, and pushes cartridge 91 onto mounting member 92. This causes (a) the penetration of stopper 99 by conduit needle 101 and (b) the penetration of citric acid compartment 97 by penetrating means 93. As indicated in relation to previous embodiments, this has the effect of establishing communication between drug compartment 95 and delivery needle 102 and also of initiating the generation of gas which will drive piston 94 to expel the liquid drug from drug compartment 95.

Continued actuation of lever 106 to the position indicated in FIG. 15 causes needle 102 to penetrate into the skin. It will be appreciated that the actuation of lever 106 accomplishes the actuation of the expelling means, the establishment of communication between the drug compartment 95 and the delivery needle 102, and the correct penetration angle and depth of delivery needle 102 into the skin. Correct and fail-safe dosing is therefore inevitable.

Figure 16:
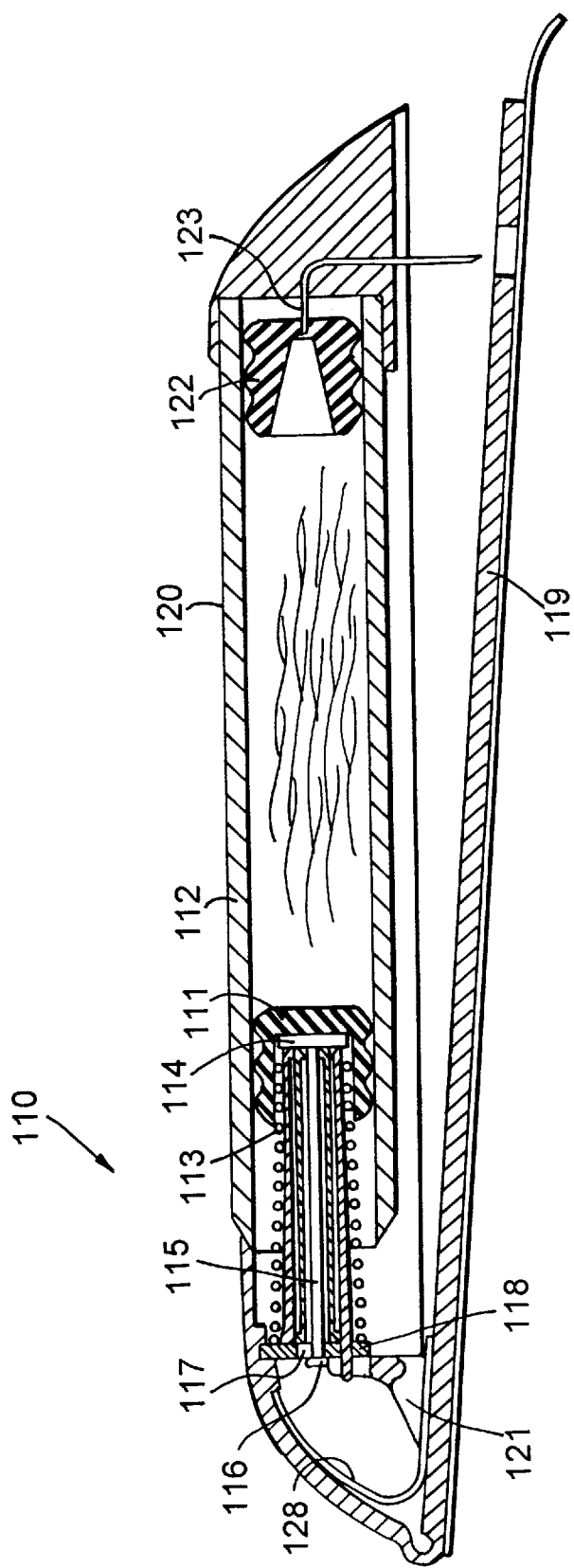
FIG. 16 is a sectional elevation of a fifth embodiment of a device according to the invention, illustrated before use.

In FIG. 16 there is indicated, generally at 110 a device similar to that of FIG. 1. Thus, it will be noted that the main components are identical and that the expelling means which drives the piston 111 along cartridge 112 comprises the spring 113 which acts on pusher plate 114 to drive the piston 111. Before use, the spring 113 is held in place by rod 115 and catch projection 116 which extends through an orifice 117 in wall section 118.

As with the device of FIG. 1, when base member 119 is placed on and adheres to the skin and pressure is exerted on top surface 120 of device 110, catch projection 116 moves relative to orifice 117 because catch projection 116 is prevented from moving downwards by abutment 121. Precompressed spring 113 causes catch projection 116 to move through orifice 117 and exerts a force on piston 111. As previously described in relation to the device of FIGS. 1–3, this force causes a stopper 122 to pierce conduit needle 123 and then causes the ejection of drug from the interior of cartridge 112.

Referring initially to FIG. 17, it can be seen that rod 115 is provided with first and second extension members 123, 124. As rod 115 moves from the starting position illustrated in FIG. 16 towards the position illustrated in FIG. 17, catch projection 116 serves to pull first extension member 123 forward and this in turn pulls the second extension member 124 forward. The second extension member 124 is provided with a projection 125 which extends through an orifice 126 in abutment 121. Projection 125 and orifice 126 act as a snap mechanism which is illustrated in greater detail in FIGS. 18 and 19. FIG. 18 shows a sectional elevation through the line A—A in FIG. 17. In FIG. 18 abutment 121, projection 125 and orifice 126 can been seen. FIG. 19 shows projection 125 and orifice 126 in greater detail. It can be seen that orifice 126 is provided with a pair of resilient teeth 127. These teeth allow projection 125 to move from the initial position as shown in FIG. 16 (and indicated in dotted outline in FIG. 19 by reference numeral 125') to the working position shown in FIG. 17 (indicated by reference numeral 125 in FIG. 19). When device 110 is applied to the skin and top surface 120 is pressed downwards, projection 125 snaps from position 125' to the position shown in FIG. 19. A spring 128 (see FIGS. 16 and 17) resists this downward movement. However, once projection 125 has snapped downwards, resilient teeth 127 prevent projection 125 from moving back up under the urging of spring 128.

Figure 20:
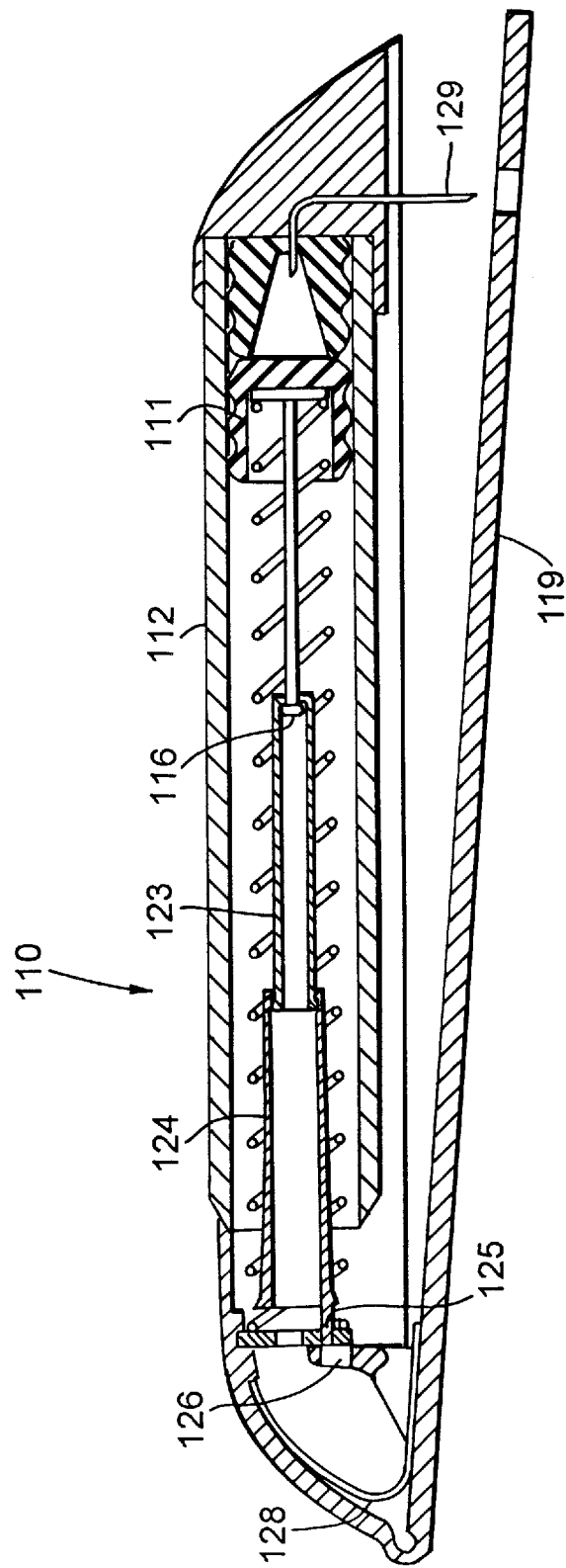
FIG. 20 illustrates the device of FIGS. 16–19, after use.

If one refers to FIG. 20, it can be seen that when piston 111 moves to its final position, catch projection 116 pulls first extension member 123 and second extension member 124 forwards to a sufficient extent that projection 125 is pulled forward and dislodged from orifice 126. This disengages the snap mechanism and allows cartridge 112 to move away from base member 119 under the influence of spring 128, to the position illustrated in FIG. 20. This has the effect of disengaging the delivery needle 129 from the skin and retracting it to a safe position. Additionally, it has the effect of indicating to the subject that delivery is completed. In use, therefore, the subject would apply device 110 to the skin, press downwards on the top surface 120 to begin delivery and shortly afterwards, top surface 120 would spring up indicating that delivery had been completed.

The same or a similar snap mechanism could be used with many of the other embodiments previously illustrated, as will be apparent to the skilled person.

Figure 21:
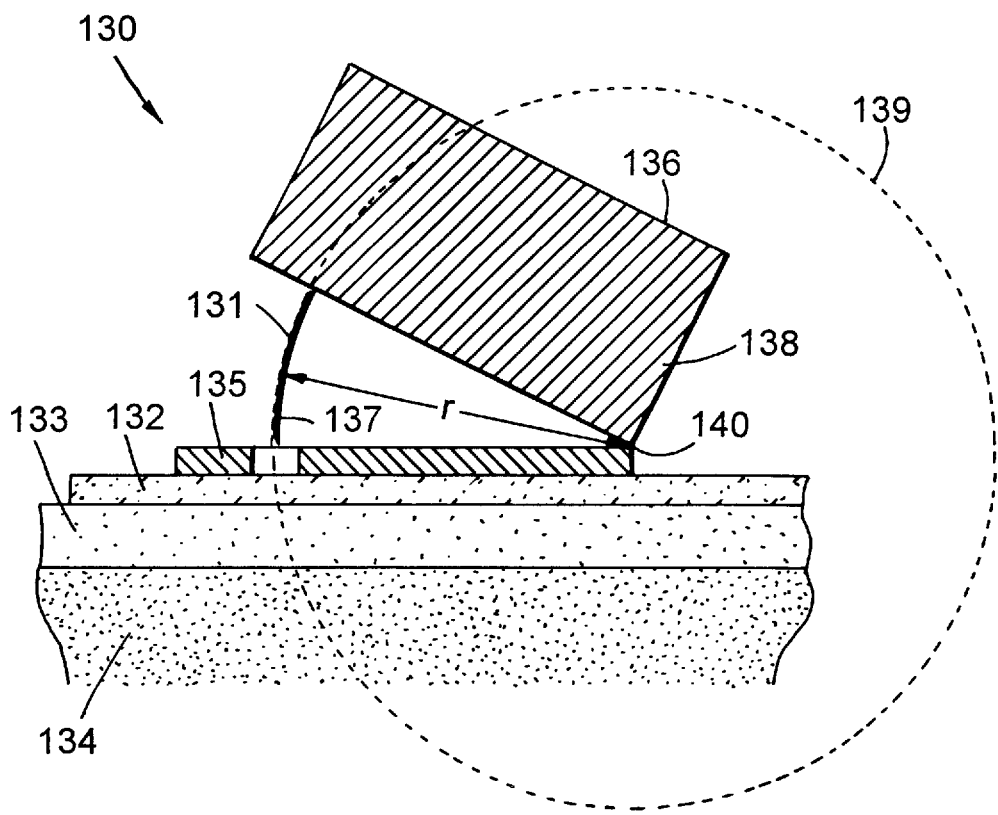
FIG. 21 is a schematic representation of a sixth embodiment of a device according to the invention.

In FIG. 21 there is indicated, generally at 130, a schematic illustration of a device according to the invention. Device 130 is designed to be used in cases where a relatively long needle is required (more specifically where there is a high ratio of needle length to distance from hinge to penetration point. For example, FIG. 21 shows a device being used for intramuscular injections, and accordingly it employs a long delivery needle 131.

Delivery needle 131 must be sufficiently long to penetrate through the skin 132, fat 133 and into muscle 134 when base section 135 is applied to a subject and top surface 136 is pushed downwards so as to cause the penetration of the skin and the actuation of the expelling means. The actual operation of the device can be the same as any of the devices previously illustrated, or can be a variant on these embodiments.

The important point to note about device 130 is that the length of needle 131 (exaggerated) causes its own problems. If needle 131 was straight, the point 137 thereof would pierce the skin and then as cartridge 138 approached base section 135, the remainder of the needle would follow the point into the skin. However, as well as entering the skin vertically (i.e. normal to the surface of the skin), the hinge mechanism gives the needle's movement a lateral component (i.e. parallel to the surface of the skin). For a long needle or a relatively small device, this lateral movement of the needle between the position in which the point penetrates the surface of the skin and the position in which the needle is fully embedded can be substantial. Instead of creating a single entry point, the needle causes the skin to stretch or tear during penetration and retraction of the needle. However, needle 131 of device 130 is provided with a curvature such that it lies along an arc of an imaginary circle 139. The centre of circle 139 is at hinge 140, and the radius or of circle 139 is equal to the distance between hinge 140 and needle 131. This curvature means that when needle 131 enters the skin, it does so at a single point and the entire needle enters the skin at the point where tip 137 penetrates the surface of the skin. The application of device 130 is therefore far less traumatic than would be the case for a device having a straight needle, and after removal, the skin and underlying tissue is less damaged than would otherwise be the case.

This type of curved needle is not just required for intramuscular injections as even subcutaneous injections may require a delivery needle of up to 10 mm in length (depending on the site to which the device is being applied.

Of course, it might be thought that the lateral movement of the needle could be reduced to a negligible amount by providing the needle closer to the hinge, and this is undoubtedly true. However, it has been found that it is advantageous to locate the needle at a point distal from the hinge as this means that when the cartridge moves towards the base member (particularly when a snap mechanism is provided) the velocity of the needle into the skin is much higher and the application of the device is, as a result, less painful.

Another reason why the needle cannot simply be placed close to the hinge in order to overcome the problems associated with lateral movement during penetration is because this places constraints on the angle of rotation between the cartridge and the skin contacting surface (e.g. in moving from the configuration of FIG. 1 to the configuration of FIG. 2). Conversely, when the needle is positioned adjacent to the hinge point, even a relatively large angle of rotation gives a limited penetration depth. For reasons of compactness during storage and transit, it is usually preferred to keep the open angle at the hinge to a minimum, i.e. to keep the device as flat as possible.

As an aid to compliance for children, the device can be provided with a housing which will appeal to children and which they will readily apply to their skin (where they would be reluctant to do with a conventional injection device).

What is claimed is:

1. A liquid drug delivery device comprising a base member defining a skin-contacting surface for application to the skin of a subject, a columnar cartridge having a longitudinal axis and an interior serving as reservoir for the drug and which is connected to the base member such that in use the longitudinal axis of the cartridge is disposed substantially parallel to the skin-contacting surface, a delivery needle communicating in use with the interior of the cartridge and adapted to penetrate the skin of the subject, and means for expelling a drug out of the interior of the cartridge and through the skin of the subject via the delivery needle.

2. A device according to claim 1, wherein a portion of the interior of the cartridge defines a drug compartment for the drug, the drug being expelled from the compartment by a piston actuated by the expelling means.

3. A device according to claim 2, wherein the interior of the cartridge also defines a chamber housing the expelling means, such that the actuation of the piston by the expelling means causes the expansion of said chamber and the contraction of said drug compartment.

4. A device according to claim 2, further comprising a conduit establishing fluid communication in use between the drug compartment and the delivery needle.

5. A device according to claim 4, wherein the conduit extends at substantially right angles from the delivery needle.

6. A device according to claim 5, wherein the conduit is integral with the delivery needle.

7. A device according to claim 4, wherein the delivery needle and the conduit form part of a needle assembly mounted on an end of the cartridge.

8. A device according to any claim 1, further comprising a mechanism for actuating the expelling means.

9. A device according to claim 1, wherein the cartridge and the base member are hinged relative to one another thereby allowing relative movement therebetween from an initial configuration to a working configuration.

10. A device according to claim 9, further comprising a mechanism for actuating the expelling means and wherein said relative movement operates the mechanism for actuating the expelling means.

11. A device according to claim 9, wherein said relative movement the hinge causes the establishment of fluid communication between the drug compartment and the delivery needle.

12. A device according to claim 9, wherein the hinge enable the cartridge and the base member to be pressed towards one another from a spaced-apart initial configuration to an adjacent working configuration.

13. A device according to claim 1, wherein the skin-contacting surface is provided with an aperture through which the delivery needle extends in use.

14. A device according to claim 1 in which a portion of the interior of the cartridge defines a drug compartment for the drag and the device is provided with a conduit enabling fluid communication to be established in use between the drug compartment and the delivery needle, wherein an end of the cartridge is provided with a stopper and the conduit and stopper are located proximate to one another, and prior to use, the conduit penetrates through the stopper and thereby establishes said communication.

15. A device according to claim 14, wherein the needle assembly is fixed with respect to the cartridge, and the stopper moves relative to both the cartridge and the needle assembly.

16. A device according to claim 15, wherein the actuation of the expelling means creates increased pressure within the drug compartment which causes the stopper to press against and penetrate the conduit.

17. A device according to claim 15, wherein the stopper is fixed with respect to the cartridge, and the needle assembly moves relative to both the cartridge and the stopper.

18. A device according to claim 1, wherein the expelling means comprises a pre-compressed spring.

19. A device according to claim 18 and further comprising a mechanism for actuating the expelling means, wherein the mechanism for actuating the expelling means comprises a catch which when released enables the pre-compressed spring to relax.

20. A device according to claim 19, wherein the connection between the cartridge and the base member allows relative movement therebetween from an initial configuration to a working configuration and wherein said relative movement causes the catch to be released.

21. A device according to claim 1, wherein the expelling means comprises a gas generator which generates a gas when two or more reactants are brought into contact.

22. A device according to claim 21, wherein the gas generator comprises at least one liquid.

23. A device according to claim 22, wherein the gas generator comprises the components of an effervescent couple.

24. A device according to claim 1, wherein the expelling means comprises a material which swells in the presence of a liquid, and also comprises a supply of said liquid.

25. A device according to claim 24, wherein said material is a swellable gel and said liquid is water.

26. A device according to claim 8 in which the expelling means comprises a material which swells in the presence of a liquid or a gas generator which generates a gas when two or more reactants, at least one reactant comprising a liquid, are brought into contact, wherein said liquid is contained within a rupturable compartment and the mechanism for actuating the expelling means comprises a penetrating member, the penetrating member and the rupturable compartment being moved relative to one another upon the relative movement of the cartridge and the base member, so as to cause the penetration of said rupturable compartment and the actuation of the expelling means.

27. A device according to claim 9, further comprising a snap mechanism which maintains a stable initial configuration and a stable working configuration and which when actuated causes the device to snap from said initial configuration to said working configuration.

28. A device according to claim 27, further comprising resilient means biasing the device to said initial configuration and means for disengaging said snap mechanism when delivery has been completed.

29. A device according to claim 28, wherein a portion of the interior of the cartridge defines a drug compartment for the drug, the drug being expelled from the compartment by a piston actuated by the expelling means and wherein said disengaging means comprises a member linked to said piston such that when the piston has completed the expulsion of drug from the drug compartment, said member is caused to move and said movement causes the disengagement of said snap mechanism, such that said resilient means causes the device to resume said initial configuration.

30. A device according to claim 29, wherein the delivery needle is in the shape of a segment of arc of an imaginary circle, said circle having a radius equal to the distance between the delivery needle and the hinge and lying in a plane which is substantially normal to the plane of the skin-contacting surface.

31. A device according to claim 1, wherein the delivery needle is straight.

* * * * *